United States Patent
Mattke et al.

(10) Patent No.: US 8,716,517 B2
(45) Date of Patent: May 6, 2014

(54) METHOD FOR PRODUCING DIISOCYANATES BY GAS-PHASE PHOSGENATION

(75) Inventors: Torsten Mattke, Freinsheim (DE); Gerhard Olbert, Dossenheim (DE); Carsten Knoesche, Niederkirchen (DE); Heiner Schelling, Kirchheim (DE)

(73) Assignee: BASF SE, Ludwigshafen (DE)

( * ) Notice: Subject to any disclaimer, the term of this patent is extended or adjusted under 35 U.S.C. 154(b) by 82 days.

(21) Appl. No.: 13/389,955

(22) PCT Filed: Aug. 10, 2010

(86) PCT No.: PCT/EP2010/061574
§ 371 (c)(1),
(2), (4) Date: Feb. 10, 2012

(87) PCT Pub. No.: WO2011/018443
PCT Pub. Date: Feb. 17, 2011

(65) Prior Publication Data
US 2012/0142959 A1    Jun. 7, 2012

(30) Foreign Application Priority Data

Aug. 11, 2009 (EP) .................................... 09167604

(51) Int. Cl.
*C07C 263/10* (2006.01)

(52) U.S. Cl.
USPC ........................................................ 560/347

(58) Field of Classification Search
USPC ........................................................ 560/347
See application file for complete search history.

(56) References Cited

U.S. PATENT DOCUMENTS

| | | | |
|---|---|---|---|
| 4,959,202 A | 9/1990 | Minet et al. | |
| 5,639,436 A | 6/1997 | Benson et al. | |
| 2007/0261437 A1* | 11/2007 | Boonstra et al. | 62/617 |
| 2007/0265466 A1* | 11/2007 | Dugal et al. | 560/347 |
| 2008/0167490 A1 | 7/2008 | Pohl et al. | |
| 2008/0260619 A1 | 10/2008 | Werner et al. | |
| 2009/0304572 A1 | 12/2009 | Sesing et al. | |
| 2010/0076218 A1 | 3/2010 | Daiss et al. | |
| 2010/0210870 A1 | 8/2010 | Olbert et al. | |
| 2010/0217035 A1 | 8/2010 | Knoesche et al. | |
| 2010/0305356 A1 | 12/2010 | Olbert et al. | |
| 2011/0105785 A1 | 5/2011 | Knoesche et al. | |
| 2011/0213178 A1 | 9/2011 | Mattke et al. | |
| 2011/0251425 A1 | 10/2011 | Penzel et al. | |
| 2011/0257428 A1 | 10/2011 | Knoesche et al. | |
| 2011/0263892 A1 | 10/2011 | Breuninger et al. | |
| 2011/0301380 A1 | 12/2011 | Knoesche et al. | |
| 2012/0004445 A1 | 1/2012 | Lehr et al. | |
| 2012/0004446 A1 | 1/2012 | Mattke et al. | |
| 2012/0016154 A1 | 1/2012 | Mattke et al. | |

FOREIGN PATENT DOCUMENTS

| | | |
|---|---|---|
| EP | 1 935 875 | 6/2008 |
| EP | 2 307 356 | 4/2011 |
| EP | 2 364 294 | 9/2011 |
| WO | 97 11026 | 3/1997 |
| WO | 2007 085476 | 8/2007 |
| WO | 2008 055899 | 5/2008 |
| WO | 2008 125236 | 10/2008 |

OTHER PUBLICATIONS

International Search Report issued on Feb. 9, 2011 in PCT/EP10/61574 filed on Aug. 10, 2010.
U.S. Appl. No. 61/220,740, filed Jun. 26, 2009, Schelling, et al.
U.S. Appl. No. 13/380,680, filed Dec. 23, 2011, Schelling, et al.
U.S. Appl. No. 13/434,135, filed Mar. 29, 2012, Lehr, et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

A process for preparing diisocyanates by gas-phase phosgenation starting out from a feed stream comprising the corresponding diamines and a phosgene-comprising feed stream, in which the feed streams are separately converted into the gas phase and preheated to the reaction temperature of the gas-phase phosgenation, wherein the waste heat from a plant for preparing chlorine by heterogeneously catalyzed oxidation of hydrogen chloride by the Deacon process is utilized for this purpose, is proposed.

22 Claims, No Drawings

METHOD FOR PRODUCING DIISOCYANATES BY GAS-PHASE PHOSGENATION

The invention relates to a process for preparing diisocyanates by gas-phase phosgenation.

Diisocyanates are prepared predominantly by phosgenation of the corresponding amines. This can be carried out either in the liquid phase or in the gas phase. In industry, the gas-phase phosgenation has a number of advantages over the liquid-phase phosgenation, in particular a higher selectivity, a lower hold-up of toxic phosgene and also lower capital and energy costs.

In the gas-phase phosgenation, the two feed streams, viz. an amine-comprising feed stream and a phosgene-comprising feed stream, are, if they are not already gaseous, vaporized and brought to the reaction temperature of the gas-phase phosgenation of about 300-400° C. This superheating and if necessary vaporization is carried out indirectly, for example by means of electric heating, by means of combustion gases or by means of high-pressure steam, in the prior art. If appropriate, a generally liquid heat transfer medium, for example a salt melt, is inserted in between. However, the provision of the high-temperature heat by known methods is very costly.

It was therefore an object of the invention to provide a process for preparing diisocyanates by gas-phase phosgenation of the corresponding amines, in which the heat required for heating and if necessary vaporizing the feed streams is provided in a technically simple manner with lower capital and energy costs.

This object is achieved by a process for preparing diisocyanates by gas-phase phosgenation starting out from a feed stream comprising the corresponding diamines and a phosgene-comprising feed stream, in which the feed streams are separately converted into the gas phase and preheated to the reaction temperature of the gas-phase phosgenation, wherein the waste heat from a plant for preparing chlorine by heterogeneously catalyzed oxidation of hydrogen chloride by the Deacon process is utilized for this purpose.

It has been found that the waste heat from a plant for preparing chlorine by heterogeneously catalyzed oxidation of hydrogen chloride by the Deacon process can advantageously be utilized for bringing the feed streams for the gas-phase phosgenation for preparing diisocyanates to the required reaction temperature of about 300-400° C. The coupling in heat terms of the Deacon process and the gas-phase phosgenation as provided for by the invention is a technically simple, elegant solution because the temperature levels are similar, i.e. the heat of reaction of the Deacon process can be utilized directly for heating the feed streams for the gas-phase phosgenation to give diisocyanates. Furthermore, coupling in terms of material is also possible:

In the gas-phase phosgenation, not only the main product, viz. the diisocyanates, but also hydrogen chloride is obtained. This can be used as starting material for oxidation to chlorine in a Deacon process. Coupling of Deacon process and gas-phase phosgenation enables capital costs for the heat management periphery in the two processes to be saved. If appropriate, the apparatuses can be constructed with a lower pressure rating, for example when using salt melts as heat transfer media.

According to the invention, the waste heat, i.e. the heat of reaction evolved in the heterogeneously catalyzed oxidation of hydrogen chloride, from a Deacon process is utilized for superheating and if necessary vaporization of the feed streams of a gas-phase phosgenation.

The invention is not restricted in terms of the specific way in which the Deacon process is carried out; in particular, this can be carried out in a fixed bed or fluidized bed.

The amine preferably has a temperature in the range from 200 to 400° C. The pressure of the amine added is preferably in the range from 0.05 to 3 bar absolute. The temperature of the phosgene added is preferably in the range from 250 to 450° C. For this purpose, the phosgene is usually heated in a manner known to those skilled in the art before addition.

Heating of the phosgene and the amine and vaporization of the amine are carried out using, for example, electric heating or direct or indirect heating by combustion of a fuel. Fuels used are usually fuel gases, for example natural gas. However, lowering the boiling point by reducing the pressure of the amine also makes heating by, for example, steam possible. The pressure of the steam is selected as a function of the boiling point of the amine. A suitable vapor pressure of the steam is, for example, in the range from 40 to 100 bar. This corresponds to a temperature of the steam in the range from 250 to 311° C.

In general, it is necessary to heat the amine to the reaction temperature in a plurality of stages. For this purpose, the amine is generally firstly preheated, then vaporized and subsequently superheated. In general, the vaporization requires the longest residence times and thus leads to decomposition of the amine. To minimize this, vaporization at low temperatures, as is obtained, for example, by means of relatively low pressure, is advantageous. To superheat the vaporized amine to reaction temperature after vaporization, heating by means of steam is generally not sufficient. Superheating is therefore usually carried out using electric heating or direct or indirect heating by combustion of a fuel.

Unlike the vaporization of the amine, the vaporization of phosgene is generally carried out at significantly lower temperatures. For this reason, it is generally possible to use steam for vaporization of the phosgene. However, the required superheating of the phosgene in order to heat it to the reaction temperature can generally only be carried out by means of electric heating or direct or indirect heating by combustion of a fuel.

The phosgene-comprising feed stream generally has a high phosgene content of almost 100% by weight together with residues of, in particular, nickel and chlorine.

The feed stream comprising diamines comprises the diamines corresponding to the desired diisocyanate target product. The diamines have to be able to be vaporized without decomposition. It is possible to use aliphatic, cycloaliphatic or aromatic diamines, preferably aliphatic diamines.

Both the phosgene-comprising feed stream and the diamine-comprising feed stream can in each case be diluted with an inert gas.

Diamines used for reaction to form the corresponding isocyanates in the process of the invention are ones in the case of which the diamine, the corresponding intermediates and the corresponding isocyanates are present in gaseous form under the reaction conditions selected. Preference is given to diamines which decompose to an extent of not more than 2 mol %, particularly preferably not more than 1 mol % and very particularly preferably not more than 0.5 mol %, during the duration of the reaction under the reaction conditions. Particularly suitable diamines are diamines, in particular diamines based on aliphatic or cycloaliphatic hydrocarbons, having from 2 to 18 carbon atoms. Examples are 1,6-diaminohexane, 1,5-diaminopentane, 1,3-bis(aminomethyl)-cyclohexane, 1-amino-3,3,5-trimethyl-5-aminomethylcyclohexane (IPDA) and 4,4'-diaminodicyclohexylmethane. Preference is given to using 1,6-diaminohexane (HDA).

It is likewise possible to use aromatic amines which can be converted into the gas phase without significant decomposition for the process of the invention. Examples of preferred aromatic amines are toluenediamine (TDA), as 2,4- or 2,6-isomer or as a mixture thereof, for example as from 80:20 to 65:35 (mol/mol) mixture, diamino-benzene, 2,6-xylidine, naphthyldiamine (NDA) and 2,4'- or 4,4'-methylene (diphenyl-diamine) (MDA) or isomer mixtures thereof. Among these, preference is given to the diamines and particular preference is given to 2,4- and/or 2,6-TDA or 2,4'- and/or 4,4'-MDA.

The invention is not restricted in respect of the specific way in which the gas-phase phosgenation is carried out. This can advantageously be carried out as in EP 2307356 by introducing the starting materials via an ejector into the reactor or by, as described in EP 2364294, cooling the reaction gas mixture from the gas-phase phosgenation in a quench with addition of a liquid quenching medium.

Preference is given to preheating the two feed streams, i.e. the diamine-comprising feed stream and the phosgene-comprising feed stream, to a temperature in the range from about 300 to 400° C., preferably to a temperature in the range from about 330 to 380° C.

The reaction gas mixture from the heterogeneously catalyzed oxidation of hydrogen chloride by the Deacon process can advantageously be utilized directly as heat transfer medium for indirect transfer of heat to the feed streams for the gas-phase phosgenation.

In a further embodiment, it is possible to utilize the temperature of the reaction gas mixture from the Deacon process for heating a secondary heat transfer medium, in particular a salt melt or steam, and to heat the starting materials for the gas-phase phosgenation by means of the secondary heat transfer medium.

The preheating and, if necessary, the conversion of the feed streams into the gas phase can be carried out in customary vaporizer constructions such as falling film evaporators, thin film evaporators or climbing film evaporators.

In one embodiment, the preheating and, if necessary, the conversion of the feed streams into the gas phase can in each case be carried out in a shell-and-tube heat exchanger, with the respective feed stream preferably being passed through the tubes of the shell-and-tube heat exchanger and the reaction gas mixture from the Deacon process or a secondary heat transfer medium being passed through the space within the shell around the tubes.

The invention claimed is:

1. A process for preparing a diisocyanate, the process comprising:
   separately vaporizing a first feed stream comprising a diamine and a second feed stream comprising phosgene, to obtain a first and a second feed stream in the gas-phase;
   separately heating the first and second feed stream in the gas-phase to a reaction temperature for gas-phase phosgenation; and subsequently
   gas-phase phosgenating the diamine to obtain the diisocyanate,
   wherein waste heat from a plant for preparing chlorine by oxidizing hydrogen chloride in the presence of a heterogeneous catalyst, the Deacon process, is utilized for the vaporizing and the heating, and
   wherein a secondary heat transfer medium is utilized as heat transfer medium for indirect heat transfer to the feed streams for the gas-phase phosgenation.

2. The process according to claim 1, wherein the gas-phase phosgenation reaction temperature is in a range from about 300 to 400° C.

3. The process of claim 1, wherein the Deacon process is carried out in a fluidized bed.

4. The process of claim 1, wherein a reaction gas mixture from the Deacon process is utilized directly as heat transfer medium for indirect heat transfer to the feed streams for the gas-phase phosgenation.

5. The process of claim 1, wherein the vaporizing and the heating are each carried out in a shell-and-tube heat exchanger, and
   each feed stream is passed through the tubes of the heat exchanger and a reaction gas mixture from the Deacon process or the secondary heat transfer medium is passed through a space within the shell and around the tubes.

6. The process of claim 1, wherein the secondary heat transfer medium is a salt melt.

7. The process of claim 1, wherein the secondary heat transfer medium is steam.

8. The process according to claim 2, wherein the gas-phase phosgenation reaction temperature is in a range from about 330 to 380° C.

9. The process of claim 2, wherein the gas-phase phosgenation reaction temperature is in a range from about 360 to 380° C.

10. The process of claim 2, wherein the Deacon process is carried out in a fluidized bed.

11. The process of claim 9, wherein the Deacon process is carried out in a fluidized bed.

12. The process according to claim 5, wherein the reaction gas mixture from the Deacon process is passed through a space within the shell and around the tubes of the exchanger.

13. The process according to claim 5, wherein the secondary heat transfer medium is passed through a space within the shell and around the tubes of the exchanger.

14. The process of claim 1, wherein the diamine is an aliphatic diamine comprising from 2 to 18 carbon atoms or a cycloaliphatic diamine comprising from 2 to 18 carbon atoms.

15. The process of claim 1, wherein the diamine is 1,6-diaminohexane or 1,5-diaminopentane.

16. The process of claim 1, wherein the diamine is 1,6-diaminohexane.

17. The process of claim 1, wherein the diamine is 1,3-bis(aminomethyl)cyclohexane, 1-amino-3,3,5-trimethyl-5-aminomethylcyclohexane, or 4,4'-diaminodicyclohexylmethane.

18. The process of claim 1, wherein the diamine is at least one selected from the group consisting of 2,4-toluenediamine and 2,6-toluenediamine.

19. The process of claim 1, wherein the diamine is at least one selected from the group consisting of a 2,4'-methylene (diphenyl diamine) and 4,4'-methylene(diphenyl diamine).

20. The process of claim 1, wherein the second feed stream consists essentially of phosgene.

21. The process of claim 1, wherein said phosgene is prepared from chlorine from said plant for preparing chlorine by the Deacon process.

22. The process of claim 1, wherein said hydrogen chloride obtained by gas-phase phosgenating said diamine is used in said plant for preparing chlorine by the Deacon process.

* * * * *